(12) United States Patent
Bokrantz et al.

(10) Patent No.: US 11,517,767 B2
(45) Date of Patent: Dec. 6, 2022

(54) GENERATING A PLURALITY OF TREATMENT PLANS FOR RADIATION THERAPY

(71) Applicant: RaySearch Laboratories AB, Stockholm (SE)

(72) Inventors: Rasmus Bokrantz, Enebyberg (SE); Martin Janson, Enskededalen (SE)

(73) Assignee: Raysearch Laboratories AB (publ), Stockholm (SE)

( * ) Notice: Subject to any disclaimer, the term of this patent is extended or adjusted under 35 U.S.C. 154(b) by 0 days.

(21) Appl. No.: 17/594,307

(22) PCT Filed: Mar. 30, 2020

(86) PCT No.: PCT/EP2020/058928
§ 371 (c)(1),
(2) Date: Oct. 11, 2021

(87) PCT Pub. No.: WO2020/207838
PCT Pub. Date: Oct. 15, 2020

(65) Prior Publication Data
US 2022/0143424 A1    May 12, 2022

(30) Foreign Application Priority Data
Apr. 12, 2019  (EP) .................................. 19168982

(51) Int. Cl.
*A61N 5/10* (2006.01)
(52) U.S. Cl.
CPC .......... *A61N 5/1031* (2013.01); *A61N 5/1043* (2013.01); *A61N 5/1045* (2013.01); *A61N 5/1081* (2013.01); *A61N 2005/1087* (2013.01)
(58) Field of Classification Search
CPC ...... G16H 20/40; G16H 30/40; A61N 5/1031; A61N 5/103; A61N 5/1045;
(Continued)

(56) References Cited

U.S. PATENT DOCUMENTS

| 7,391,026 B2 | 6/2008 | Trinkaus et al. |
| 2013/0304503 A1* | 11/2013 | Kuefer ................... A61N 5/103 705/2 |
| 2019/0001152 A1* | 1/2019 | O'Connor .............. G06V 10/25 |

FOREIGN PATENT DOCUMENTS

| CN | 107073284 A | 8/2017 |
| CN | 107847757 A | 3/2018 |

(Continued)

OTHER PUBLICATIONS

International Search Report. International application No. PCT/EP2020/058928. Patent Cooperation Treaty. European Patent Office, P.B. 5818 Patentlaan 2, NL—2280 HV Rijswijk. international search report: dated Jun. 26, 2020. p. 3.

(Continued)

*Primary Examiner* — Christine H Matthews
*Assistant Examiner* — Joshua Daryl D Lannu
(74) *Attorney, Agent, or Firm* — Noréns Patentbyrå AB

(57) ABSTRACT

It is provided a method for generating a plurality of treatment plans for radiation therapy, each treatment plan specifying weights for a plurality of geometrically defined fluence elements. Each weight defines an amount of radiation fluence, to thereby provide radiation dose to a target volume. The method is performed in a treatment planning system and comprises the steps of: generating a first set of treatment plans; determining a subset of the fluence elements, based on the first set of treatment plans; and generating a second set of at least two treatment plans, wherein the treatment plans only contain weights for the subset of fluence elements.

18 Claims, 3 Drawing Sheets

(58) Field of Classification Search
CPC .......... A61N 2005/1041; A61N 5/1037; A61N 5/1038; A61N 5/1039; A61N 5/1036; A61N 5/1047; A61N 2005/1091; A61N 2005/1092; A61N 5/1042; A61N 5/1071; A61N 5/1077; A61N 2005/1087; A61N 2005/1089; A61N 5/10; A61N 5/1081
See application file for complete search history.

(56) References Cited

FOREIGN PATENT DOCUMENTS

| | | | |
|---|---|---|---|
| CN | 108697905 A | 10/2018 | |
| EP | 3421085 A1 * | 1/2019 | ............. A61N 5/103 |
| EP | 3421085 A1 | 1/2019 | |
| WO | 2017041194 A1 | 3/2017 | |

OTHER PUBLICATIONS

Office action dated Jul. 15, 2022 in corresponding Chinese patent application No. 202080026355.1, incl. English translation.

* cited by examiner

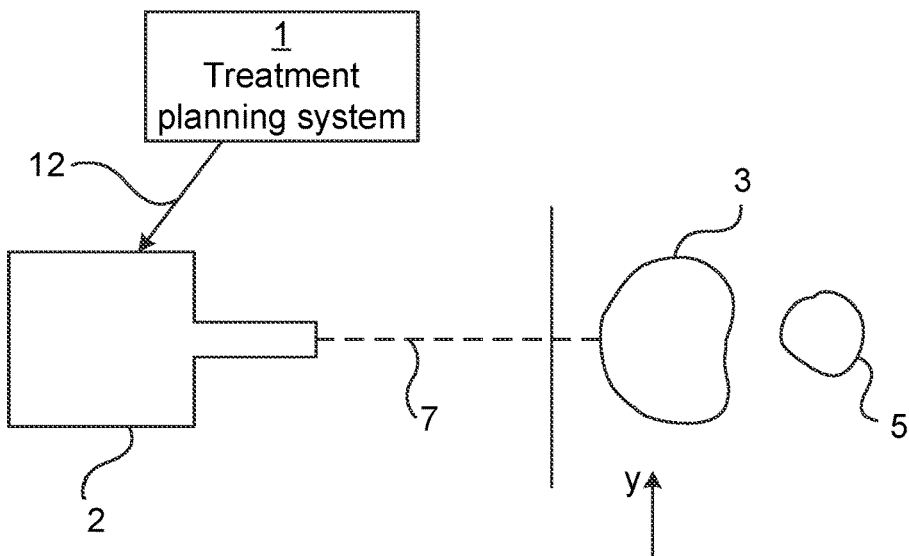
Fig. 1
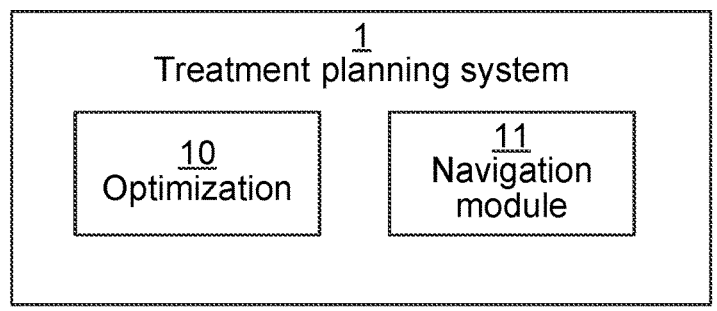
Fig. 2
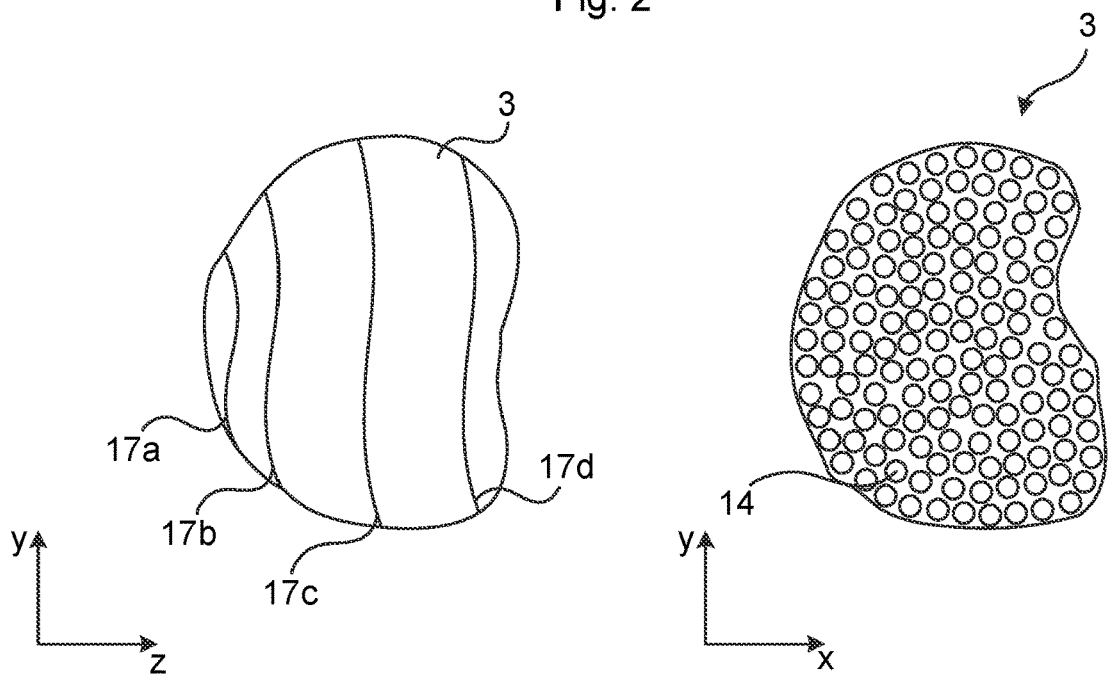
Fig. 3
Fig. 4

GENERATING A PLURALITY OF TREATMENT PLANS FOR RADIATION THERAPY

TECHNICAL FIELD

The present disclosure relates to the field of radiation therapy and in particular to generating such plans while restricting to a subset of fluence elements.

BACKGROUND

Multi-criteria optimization (MCO), also referred to as multi-objective optimization, for radiation therapy planning is a development that allows users to modify a navigated dose distribution, e.g. through a set of slider bars, where each slider bar represents a criterion affecting the dose distribution. The navigated dose is a convex combination of the dose distributions for a pre-calculated set of base plans (a convex combination is a weighted average where the weights are nonnegative and sum to one). The navigated dose distribution is updated in real-time based on the current slider positions. The navigation is directly deliverable if the navigated dose distribution can be recreated exactly by a feasible treatment plan, i.e. a plan that takes all limitations of the delivery system with respect to the plan parameters into account.

Directly deliverable navigation for scanned ions is non-trivial despite that the relationship between physical dose and spot weights is linear. Linearity means that the convex combination of the spot weights of the base plans, where the convex coefficients are identical to those used for the navigated dose distribution, defines a treatment plan that exactly recreates the navigated dose distribution. These navigated spot weights must, however, satisfy certain limits that require each weight to either be zero or between some lower and upper bound. These bounds may be fixed or depend on beam energy. For ion delivery system supporting continuous scanning, the spot weight bounds may also depend on the length of the spot segment. The navigated spot weights are in general not feasible with respect to the limits even if all the spot weights of the base plans are feasible.

The delivery of arc-based photon beam radiation therapy, such as tomotherapy and volumetric modulated arc therapy (VMAT), is also governed by weights for fluence elements that must satisfy limits that require each weight to either be zero or between some lower and upper bound. Similar to the ion beam therapy case, navigated fluence weights are in general not feasible with respect to the limits even if all fluence weights of the base plans are feasible.

In the prior art, post-processing can be used to arrive at a deliverable treatment plan. For example, navigated spot weights that are infeasible with respect to the spot weight limits are rounded to the closest feasible value. Such post-processing causes the dose distribution of the deliverable plan deviate from the navigated dose distribution. The need to compensate for discrepancies between the navigated dose distribution and the dose distribution of the deliverable plan can make the treatment planning workflow a time-consuming trial and error process.

A method of computer-assisted customization of a dose distribution plan is disclosed in US20130304503A1. Departing from an initial plan, a user specifies a new dose value for a local group of voxels, which may be a small fraction (5% or less) of the total volume covered by the initial plan. The purpose may be to avoid a local overdosing in a risk area or a local under-dosing in a target area. The initial plan is then converted, in substantially the same manner as the initial plan was, into a navigation plan which has the specified new dose value. Because the initial plan is only locally changed, the initial plan is practically maintained. A convex combination of the initial plan and the navigation plan derived therefrom may be visualized together with input means allowing a user to vary the weight of each plan.

SUMMARY

One objective is to improve how a deliverable treatment plan is achieved.

According to a first aspect, it is provided a method for generating a plurality of treatment plans for radiation therapy, each treatment plan specifying weights for a plurality of geometrically defined fluence elements. Each weight defines an amount of radiation fluence, to thereby provide radiation dose to a target volume. The method is performed in a treatment planning system and comprises the steps of: generating a first set of treatment plans; determining a subset of the fluence elements, based on the first set of treatment plans; and generating a second set of at least two treatment plans, wherein the treatment plans only contain weights for the subset of fluence elements.

Each non-zero weight of a fluence element in the second set of treatment plans may be greater than or equal to a minimum weight.

Generating the second set of two treatment plans may include applying a constraint that fluence elements outside the subset shall be zero.

The first set of treatment plans may be a result of optimization with respect to a first multi-criteria optimization problem and the second set of treatment plans may be a result of optimization with respect to a second multi-criteria optimization problem. The second multi-criteria optimization problem may differ from the first multi-criteria optimization problem by a constraint that fluence elements outside the subset shall be zero.

The method may further comprise the step of using the second set of treatment plans in an operator navigation system, which comprises calculating a navigated dose distribution by interpolation of dose distributions associated with the second set of treatment plans.

The step of using the second set of treatment plans in the operator navigation system may comprise providing a graphical user interface visualizing the navigated dose distribution and a navigation control interface, the navigation control interface allowing an operator to adjust the navigated dose distribution.

The step of determining a subset of the fluence elements may comprise discarding fluence elements having a statistical measure less than a threshold weight, the statistical measure being calculated for each fluence element across all treatment plans in the first set of treatment plans.

The statistical measure may comprise a mean value and/or a percentile value.

The step of determining a subset of the fluence elements may comprise ensuring there is a sufficient density of fluence elements across the whole target volume. An effect of this is that a sufficient dose to the entire target volume, such as a tumor, is guaranteed; this may correspond to complete elimination of all clonogenic tumor cells.

Each treatment plan may be configured to be delivered using a scanned ion beam, wherein each fluence element is associated with a scanning spot of the beam, the scanning spot being defined by a scan position for the beam and a beam energy.

Each treatment plan may be configured to be delivered using a radiation beam collimated by a binary multi-leaf collimator (MLC), wherein each leaf of the MLC can alternate between an open and a closed position. Each fluence element is then associated with a particular leaf of the MLC at a particular incidence direction of the beam relative to the target volume.

Each treatment plan may be configured to be delivered using a radiation beam collimated by an MLC, wherein the leaves of the MLC are arranged into opposed leaf pairs and each leaf can assume any one of a plurality of positions between a minimum and a maximum position. Henceforth, such an MLC is called a "continuous MLC." Each fluence element is then associated with a bixel, each bixel being a surface element in a cross-section of the beam at a particular incidence direction relative to the target volume.

Each incidence direction of the radiation beam relative to the target volume may be determined by either or both of a rotating gantry and a moveable couch.

Each treatment plan may be configured to be delivered with the incidence direction of the radiation beam relative to the target volume changing during the course of the delivery.

According to a second aspect, it is provided a treatment planning system for generating a plurality of treatment plans for radiation therapy, each treatment plan specifying weights for a plurality of geometrically defined fluence elements, each weight defining an amount of radiation fluence, to thereby provide radiation dose to a target volume. The treatment planning system comprises: a processor; and a memory storing instructions that, when executed by the processor, cause the treatment planning system to: generate a first set of treatment plans; determine a subset of the fluence elements, based on the first set of treatment plans; and generate a second set of at least two treatment plans, wherein the treatment plans only contain weights for the subset of fluence elements.

According to a third aspect, it is provided a computer program for generating a plurality of treatment plans for radiation therapy, each treatment plan specifying weights for a plurality of geometrically defined fluence elements, each weight defining an amount of radiation fluence, to thereby provide radiation dose to a target volume, the computer program comprising computer program code which, when run on a treatment planning system causes the treatment planning system to: generate a first set of treatment plans; determine a subset of the fluence elements, based on the first set of treatment plans; and generate a second set of at least two treatment plans, wherein the treatment plans only contain weights for the subset of fluence elements.

According to a fourth aspect, it is provided a computer program product comprising a computer program according to claim the third aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

Aspects and embodiments are now described, by way of example, with reference to the accompanying drawings, in which:

FIG. 1 is a schematic drawing illustrating an environment in which embodiments presented herein can be applied;

FIG. 2 is a schematic diagram illustrating functional modules of the treatment planning system of FIG. 1 according to one embodiment;

FIG. 3 is a schematic drawing illustrating the position of the Bragg peak for the different energy layers of the target volume of FIG. 1;

FIG. 4 is a schematic drawing illustrating the lateral distribution of spots in one of the energy layers of FIG. 3 according to one embodiment;

DETAILED DESCRIPTION

Figure 5:
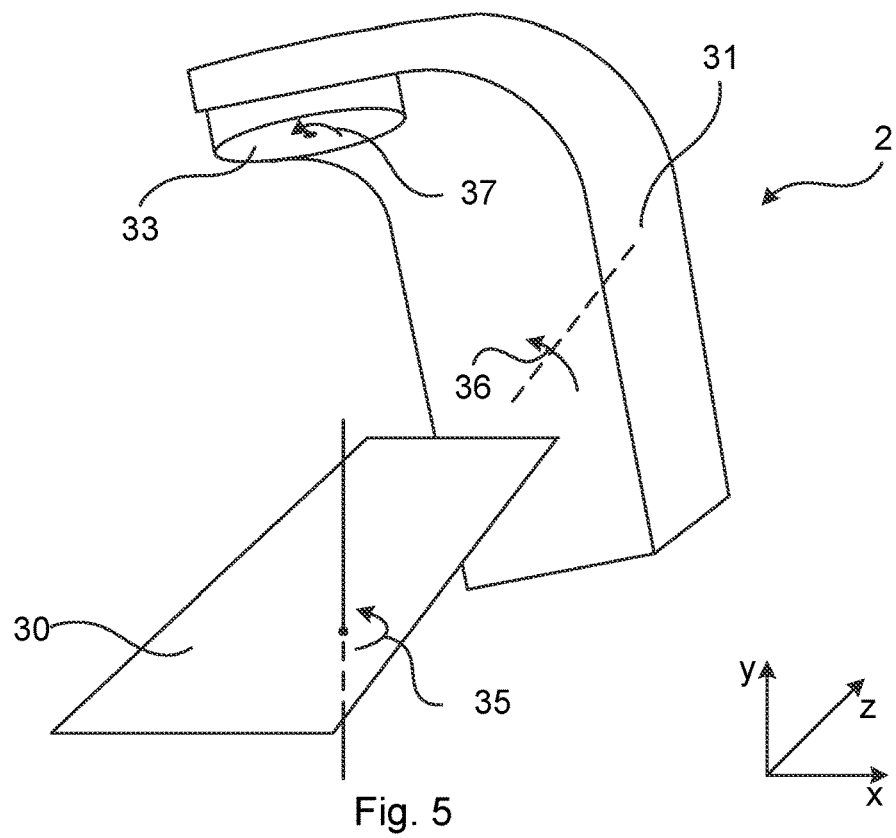
FIG. 5 is a schematic perspective view of a treatment machine, illustrating a radiation delivery system employing a continuous MLC.

The aspects of the present disclosure will now be described more fully hereinafter with reference to the accompanying drawings, in which certain embodiments of the invention are shown. These aspects may, however, be embodied in many different forms and should not be construed as limiting; rather, these embodiments are provided by way of example so that this disclosure will be thorough and complete, and to fully convey the scope of all aspects of invention to those skilled in the art. Like numbers refer to like elements throughout the description.

FIG. 1 is a schematic drawing illustrating an environment in which embodiments presented herein can be applied. A treatment planning system 1 determines how radiation is to be delivered to a target volume 3. More specifically, the treatment planning system supplies a treatment plan 12 to a radiation delivery system 2. The treatment plan 12 specifies weights for a plurality of geometrically defined fluence elements. Each weight defines an amount of radiation fluence, to thereby provide radiation dose to the target volume 3. There may be an organ at risk 5 in proximity to the target volume 3. In that case, the treatment plan is determined with a balance between sufficient dose delivery to the target volume 3 while keeping dose delivery to the organ at risk 5 low.

The way in which the radiation delivery system 2 generates the beam and delivers the dose differs depending on the treatment modality (such as photons, electrons, or ions) and geometric configuration, as is well known in the art per se. However, the common goal is to deliver a dose to the target volume 3 (i.e. the tumor) that is as close as possible to a prescribed dose while minimizing the dose to organs at risk 5, which depends on where the tumor is located.

In an ion beam embodiment, explained in more detail below with reference to FIGS. 3 and 4, the treatment plan is delivered using a scanned ion beam. In that case, each fluence element is associated with a scanning spot of the beam. The scanning spot is defined by a lateral scan position for the beam and a beam energy. For ion delivery system supporting continuous scanning, the fluence element of a spot is defined as the fluence delivered between two scan positions. The treatment plan is made up of a set of energy layers, each containing a distribution of scanning spots for ion beam therapy. This is communicated as a treatment plan 12 to an ion beam system. Based on the treatment plan 12, the ion beam system generates an ion beam 7 that is scanned spot by spot over the target volume 3 of a patient. Each scanning spot generates a spot dose distribution in the target volume 3 of the patient. In the coordinate system indicated in FIG. 1, depth is represented along a z-axis and the y-axis is upwards. The view in FIG. 1 can thus be considered to be a side view. The location of the dose maximum (Bragg peak) of a spot dose distribution depth-wise, i.e. along the z-axis, is controlled by the kinetic energy of the ions; higher energy results in a deeper location of the dose maximum. Moreover, the lateral position, along the y-axis and x-axis (not shown in FIG. 1), is controlled using electromagnets to deflect the beam 7. In this way, scanning spots can be provided to achieve a dose distribution covering the target volume 3 in three dimensions.

In an arc-based photon beam radiation therapy embodiment, explained in more detail below with reference to FIGS. 5 and 6, the treatment plan is delivered during rotational movement of the machine gantry and/or patient couch. Moreover, the patient couch can be subject to translational movements during the course of the delivery. The positions of the machine gantry and patient couch at any one time defines an incidence direction. In one embodiment, the treatment machine is equipped with a binary MLC. While moving, the configuration of the binary MLC can be adjusted by having each leaf fully open or fully closed, i.e. in a binary configuration. Each treatment plan is then delivered using a radiation beam collimated by the binary MLC, such that each leaf of the MLC can alternate between an open and a closed position. In this embodiment, each fluence element is associated with a particular leaf of the MLC at a particular incidence direction of the beam relative to the target volume. In another embodiment, instead of the binary MLC, the MLC can be a continuous MLC, in which the leaves can assume any one of a plurality of positions between a maximum position (e.g. fully open) and a minimum position (e.g. fully closed). In this embodiment, each fluence element is associated with a bixel, which is a surface element in a cross-section of the beam at a particular incidence direction relative to the target volume. As explained in more detail below, each incidence direction of the radiation beam relative to the target volume is determined by either or both of a rotating machine gantry and a moveable patient couch.

FIG. 2 is a schematic diagram illustrating functional modules of the treatment planning system of FIG. 1 according to one embodiment.

The treatment planning system comprises an optimization module 10 and a navigation module 11. Each of these modules 10, 11 can be implemented in software.

The optimization module 10 creates several base plans which are optimized for different criteria, such as total dose, local dose, minimum/maximum dose, dose in sensitive tissue, number of projections. According to embodiments presented below, the base plans correspond to the second set of treatment plans.

The navigation module 11 allows the user to modify a navigated dose distribution through a set of slider bars, where each slider bar represents a criterion affecting the dose distribution. As is well known per se in the field of graphical user interfaces (GUIs), a slider bar is an element allowing a user to set, modify and/or view a current value of a scalar quantity. It is furthermore known that the slider bar is but one example of elements with this ability; the scope of the present invention is not restricted to slider bars but encompasses any equivalent GUI element. The navigated dose distribution is a convex combination of the dose distributions for the set of base plans. Each base plan may correspond to particular emphasis on one of the criteria; this may correspond to one of the objective functions of the MCO. The navigated dose distribution is updated in real-time based on the current slider positions. The updating may include recalculating the convex combination but normally does not require for the MCO to be solved anew. Each slider may be associated with a criterion; increasing the slider corresponds to giving more weight in the convex combination to the base plan with particular emphasis on that criterion. According to embodiments presented herein, the navigated dose distribution is directly deliverable by the radiation delivery system.

FIG. 3 is a schematic drawing illustrating the Bragg peak positions of the energy layers of the target volume 3 of FIG. 1 when radiation is delivered using a scanned ion beam. FIG. 3 is a side view, from the same perspective as the view of FIG. 1. As explained above, the depth of the Bragg peak depends on energy level. Here, the Bragg peak depths of four energy levels 17a-d are shown in the target volume 3. A first energy level 17a is illustrated by a line where the Bragg peaks occur for that energy level when ions of a first amount of energy, but with different lateral deflections are supplied using the ion beam therapy in the system of FIG. 1. A second energy level 17b is illustrated by a line where the Bragg peaks occur when ions of a second amount of energy are supplied, etc. It is to be noted that the density of tissue that the ion beam passes through affects the depth. For instance, if the beam passes through bone this results in a different depth of the Bragg peak than if the beam passes through only soft tissue. Consequently, the Bragg peak depth of each energy level 17a-d does not need to be a straight line of a certain depth.

FIG. 4 is a schematic drawing illustrating the lateral distribution of scanning spots in one of the energy layers (see 17a-d) of FIG. 3 according to one embodiment. The energy layer is shown along an x-y plane. While the energy layer does not need to be completely flat in the target volume of the patient, the energy layer is here depicted as a flattened layer.

Scanning spots 14, illustrated as circles in FIG. 4, are provided throughout the energy layer to cover the target volume 3 at that energy layer. The weight, which can e.g. be applied by controlling the scanning time at a certain spot, can differ between scanning spots. The weight of each scanning spot must be greater than or equal to a minimum spot weight, which may be dependent on how fast a kicker magnet is able to open and close the beam line of the ion beam delivery system.

While FIG. 4 only discloses the distribution of scanning spots in one energy layer, there are corresponding distributions of scanning spots for each energy layer to be used for a target volume.

FIG. 5 is a schematic perspective view of a treatment machine, illustrating a radiation delivery system for arc-based radiation therapy. A Cartesian coordinate system in dimensions x, y, and z is also shown. It is to be noted that this coordinate system differs from the coordinate system of FIG. 1, FIG. 3 and FIG. 4.

A gantry 31 is rotatable around a gantry axis which is here parallel to the z-axis. A gantry angle 36 defines the extent of the gantry rotation. It is not important from where the gantry angle 36 is defined, as long as this definition is consistent.

A couch 30 is provided on which the patient (not shown) lies during treatment. Various fixation mechanisms, known per se, can be applied to ensure the patient and the treatment volume is fixated in a known position. The couch 30 is rotatable around a couch axis which is here parallel to the y axis. A couch angle 35 defines the extent of the couch rotation. It is not important from where the couch angle 35 is defined, as long as this definition is consistent. Furthermore, the couch may be movable in the z direction.

An MLC 33 is provided mounted to the gantry 31, through which the radiation is provided during treatment. The MLC 33 can be rotatable around a collimator axis. The collimator axis varies in its orientation (of the Cartesian coordinate system) depending on the rotation of the gantry 31. A collimator angle 37 defines the extent of the rotation of the MLC. It is not important from where the collimator angle 37 is defined, as long as this definition is consistent.

A combination of values of the couch angle 35, the gantry angle 36 and optionally the collimator angle 37 define an incidence direction. The incidence direction defines at what angle radiation will treat the patient. A beam plane is a normal plane to a beam direction, i.e. the collimator axis.

Each trajectory occurs in an arc from a start time to an end time and defines motion between incidence directions. In one embodiment, the motion is in a helical form for helical tomotherapy, in which case translational movement between the couch and the gantry is enabled along the z-axis.

Tomotherapy is a form of photon beam therapy where the patient is irradiated by a slit beam that rotates continuously around the patient. The rotation is discretized into a number of projections for planning purposes (normally 51 projections per rotation). The width of the slit is defined by a pair of movable jaws, with typical widths being 0.5 to 5 cm, and the irradiation through the slit is collimated by a set of pneumatically driven MLC leaves. The collimation introduced by the leaves can be binary in the sense that the leaves can only be either completely open or completely closed. For embodiments presented herein, the weights of the fluence elements correspond to the open times of the MLC leaves at a particular incidence direction. The weights, i.e. the leaf open times, need to be greater than or equal to a lower bound for all open MLC leaves. The lower bound corresponds to the minimum leaf open time, which may be dependent on the shortest possible time a leaf can be in open configuration due to the finite leaf speed of the MLC. A weight of zero, which corresponds to a closed leaf, is also possible. Weights between consecutive projection must also satisfy a minimum (non-zero) close time constraint. A close time of zero is also possible because a leaf need not close between two consecutive projections.

In one embodiment, the motion is performed for VMAT. The arc trajectory defines a motion implemented using a change in one or more of the couch angle 35, the collimator angle 37, and the gantry angle 36. The MLC is here in a continuous configuration, in which each leaf of the MLC can assume any one of a plurality of positions between a fully open and a closed position. The leaf positions for the continuous MLC are generally controlled by mechanical motors. The leaves are also arranged into opposed leaf pairs. In this case, each fluence element is associated with a bixel, which is a surface element in a cross-section of the beam (i.e. the beam plane) at a particular incidence direction relative to the target volume. The surface element may correspond to the smallest controllable unit of the MLC, such as one leaf or leaf pair. For embodiments presented herein, the weight of a fluence element, i.e. a bixel weight, correspond to the amount of radiation fluence that is delivered while the bixel is not blocked by the MLC leaves. The bixel weight must be greater than or equal to a lower bound, which may dependent on the minimum tip gap between opposed leaves and a finite maximum leaf speed. Bixel weights of zero may also be feasible, corresponding to bixels that are always shielded by the MLC leaves.

In one embodiment, radiation is turned on for the whole duration of each arc trajectory. The speed of motion during the arc trajectory can be constant or can vary.

Figure 6:
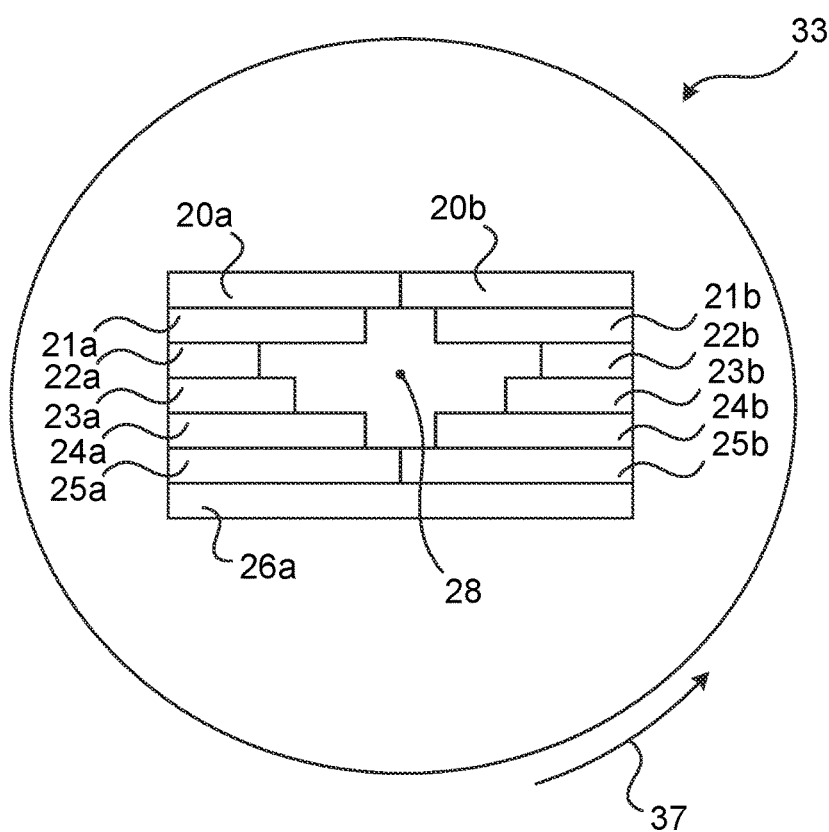
FIG. 6 is a schematic drawing illustrating the MLC of FIG. 5.

FIG. 6 is a schematic drawing illustrating the MLC 33 of FIG. 5, when applied in continuous configuration. The MLC 33 comprises pairs of leaves 20a-b, 21a-b, ..., 26a-b. Each leaf is movable in one dimension only.

Each pair of opposing leaves can be positioned to provide a space in between the leaves. In this way, an opening 28 can be defined through which radiation can flow. The opening 28 can be tailored to cover a target volume 3, while reducing radiation to surrounding tissue. Since the leaves 20a-b, 21a-b, ..., 26a-b are only movable along a single dimension, the possible shapes of the opening 28 depend on the rotation angle 37 of the MLC 33. When the MLC 33 is in a binary configuration, each leaf can only rest in a fully open position or a fully closed position. For the binary configuration, there may be leaf pairs, similar to what is shown in FIG. 6, or there may be only one leaf per configurable opening, corresponding to each vertical position in FIG. 6.

Figure 7:
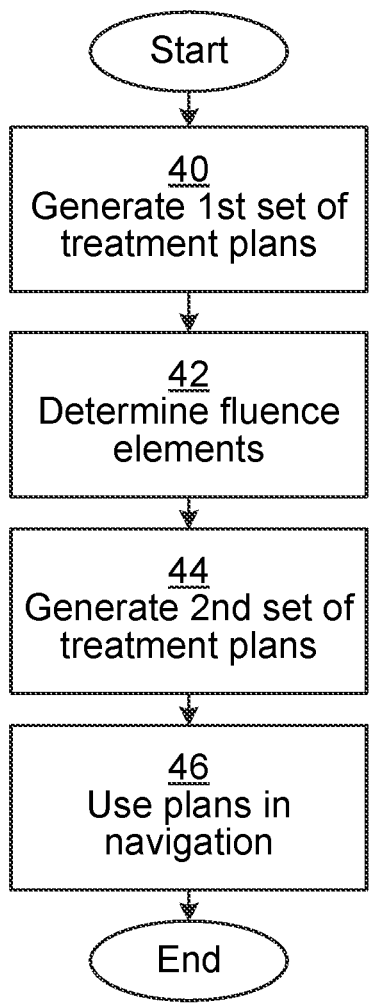
FIG. 7 is a flow chart illustrating embodiments of methods for generating a plurality of treatment plans for radiation therapy, the method being performed in the treatment planning system of FIG. 1.

FIG. 7 is a flow chart illustrating embodiments of methods for generating a plurality of treatment plans for radiation therapy. The methods are performed in the treatment planning system of FIG. 1. Each treatment plan specifies weights for a plurality of geometrically defined fluence elements. Furthermore, each weight defines an amount of radiation fluence, to thereby provide radiation dose to a target volume.

In a generate $1^{st}$ set of treatment plans step 40, the treatment planning system generates a first set of treatment plans. In the generation of the first set of treatment plans, these are generated with respect to an initial set of fluence elements being selected equal for all plans in the first set of treatment plans. Moreover, the plans are generated without consideration to any (non-zero) minimum weight for the fluence elements. Nevertheless, a consideration of a maximum weight can be included in the generation of the first set of treatment plans. The first set of treatment plans may be the result of optimization with respect to a first multi-criteria optimization problem, wherein a number of different objective functions may be used (sequentially). Each treatment plan in the first set of treatment plans can represent a particular optimization criterion, or a particular weighting of more than one criterion. The particular optimization criterion may be expressed in terms of the objective function that is used to generate that treatment plan and/or in terms of a constrained applied.

In a determine fluence elements step 42, the treatment planning system determines a subset of the fluence elements, based on the first set of treatment plans. This can comprise discarding fluence elements having a statistical measure less than a threshold weight. The statistical measure is calculated for each fluence element across all treatment plans in the first set of treatment plans. For instance, the statistical measure can comprise a mean value or a percentile value. In this way, fluence elements which e.g. have too little weight (measured as mean value or a percentile value) across the treatment plans in the first set, are discarded since their contribution to the treatment plans is too small and may be under the minimum weight to be deliverable.

Optionally, this step comprises ensuring there is a sufficient density of fluence elements across the whole target volume. Such optional ensuring may be applied after the comparison with the threshold weight but before the decision-making, whereby fluence elements which are important to maintain a sufficient density are excepted from discarding. Hence, fluence elements that might have been discarded, if the preceding comparison with threshold weight had been applied exclusively, are effectively not discarded when the optional additional aim to keep a set of fluence elements that provides sufficient coverage for the target volume is taken into account.

A possible process implementing the determine fluence elements step 42 will now be described. In a first substep, a reference coverage is computed for each treatment plan in the first set of treatment plans or collectively for all treatment plans in the first set of treatment plans. The reference coverage may be computed as a volume-at-dose, i.e., the volume $\mu(V_d)$ of an identified region $V_d$ of the target volume V which receives a least dose d:

$$V_d = \{x \in V : D(x) \geq d\},$$

where D (x) denotes the dose at point x according to the treatment plan(s) in the first set. The set $V_d$ can be defined with respect to a least dose d which is suitable in view of the treatment to be delivered, e.g., 90% or 95% or 100% of a prescription dose $D_p$. For example, if the prescription dose is $D_p$=60 Gy, the reference coverage may be the volume of the region $V_{56\ Gy}$. If the first set contains multiple treatment plans, the reference coverage may be the minimum, maximum, median or average volume-at-dose over the first set. Alternatively, the volume-at-dose may be computed on the basis of a combination (e.g., convex combination, linear interpolation) of at least some of the treatment plans in the first set. In particular, such combination may be a balanced treatment plan in view of clinical, biological or technical desirability factors.

In a second substep, the treatment planning system determines a subset F of the fluence elements, as described above.

In a third substep of step 42, it is determined whether the reference coverage can be achieved using the subset F of the fluence elements. The reference coverage may be considered to be non-achievable if too many points or voxels in $V_d$ lie outside the region $I_F$ which is irradiable by the subset F of the fluence elements. This may be assessed by applying the following quantitative criterion, requiring that at least a fraction $\gamma$ of the region $V_d$ shall remain irradiable:

$$\frac{\mu(V_d \cap I_F)}{\mu(V_d)} \geq \gamma.$$

In this expression, one may for example apply $\gamma$=0.90 or $\gamma$=0.95 or even $\gamma$=1. In general, a higher value of $\gamma$ will tend to increase the number of fluence elements belonging to the subset F, in which the treatment plans in the second set are allowed to contain weights. If it is determined that a too small fraction of the region $V_d$ is irradiable by the subset F of fluence elements, the treatment planning system repeats the determination of a subset of the fluence elements, however, with different initial values, a different randomization (e.g., random seed) or adjusted parameters. Adjusting the parameters may for example include decreasing the threshold weight which is used in the above-described process of discarding fluence elements having a statistical measure less than the threshold weight. The threshold weight may be decreased by a fixed factor equal to couple of percent, one percent or a fraction of a percent; this may be a balance between processing time and accuracy which is desirable in view each particular implementation. Then, the comparison with the decreased threshold weight is performed and it is verified whether the reference coverage is achievable using the resulting new subset F' of fluence elements; this may include applying the $\gamma$-dependent quantitative criterion above. If the reference coverage is achievable, the new subset F' will form the output of step 42.

Still under the third substep of step 42, an alternative reaction to a determination that some points or voxels in the region $V_d$ cannot be irradiated by the subset of the fluence elements is the following: The treatment planning system searches for additional fluence element which were used in some of the first set of treatment plans and which, if restored into the subset, will render a larger fraction of the region $V_d$ irradiable again. The search may be restricted to fluence elements on or adjacent to the boundary of the subset of fluence elements. Such boundary may be a point set (or discretized point set) in a two-dimensional representation of the fluence elements. Then, the final output of step 42 may include one or more additional fluence elements from this set. In other words, these additional fluence elements are effectively not discarded when the optional additional aim to keep a set of fluence elements that provides sufficient coverage for the target volume is taken into account. To summarize, the behavior of this optional implementation of step 42, which includes ensuring there is a sufficient density of fluence elements across the whole target volume, is mainly controlled by the values assigned to parameters d and $\gamma$ and, if applicable, by the way of collectively computing the volume-at-dose.

In a generate $2^{nd}$ set of treatment plans step 44, the treatment planning system generates a second set of at least two treatment plans. These treatment plans only contain weights for the subset of fluence elements, and the weight for each fluence element in the subset of fluence elements is constrained to satisfy the minimum and maximum weight requirements. Each treatment plan in the second set may correspond to a treatment plan in the first set. Such correspondence may include that an identical objective function is used, or that an objective function only modified to include the minimum weight requirement is used. The second set of treatment plans may be the result of optimization with respect to a second multi-criteria optimization problem.

The second multi-criteria optimization problem may differ from the first multi-criteria optimization problem in that it includes a constraint that fluence elements outside the subset shall be zero. As is well known to the person skilled in the art, such constraint may be expressed in terms of a change to the objective function, e.g., by the addition of a barrier-function term. In one embodiment, the zero constraint applies to all fluence elements in the target volume except for the subset. In another embodiment, the zero constraint applies to those fluence elements which are such that (i) the fluence element had a non-zero weight in any of the first set of treatment plans and (ii) the fluence element is outside the determined subset.

In one embodiment, each non-zero weight of a fluence element in the second set of treatment plans is greater than or equal to a minimum weight, and less than or equal to a maximum weight. The minimum weight and the maximum weight can be determined based on physical limitations of the radiation delivery system. In the case of the ion beam embodiment, the fluence element is a scanning spot. In the case of the tomotherapy embodiment, the fluence element corresponds to a particular leaf of the MLC at a particular incidence direction of the beam relative to the target volume. In the case of the VMAT embodiment, the fluence element corresponds to a bixel being a surface element in a plane perpendicular to a particular incidence direction of the beam relative to the target volume.

In a use plans in navigation step 46, the treatment planning system uses the second set of treatment plans in an operator navigation system, such as the navigation module described above and shown in FIG. 2. This comprises calculating a navigated dose distribution by interpolation of dose distributions associated with the second set of treatment plans. The interpolation can e.g. be implemented by means of forming convex combinations of the dose distributions associated with the second set of treatment plans. This can comprise providing a graphical user interface visualizing the navigated dose distribution. In this case, a navigation control interface is also provided. The navigation control interface allows an operator to adjust the navigated dose distribution, e.g. using slider bars.

The first set of treatment plans can be a result of optimization with respect to a first multi-criteria optimization problem, while the second set of treatment plans can be a result of optimization with respect to a second multi-criteria optimization problem. In other words, the optimization problems can differ between the first set and the second set of treatment plans.

As explained above, in one embodiment, each treatment plan is configured to be delivered using a scanned ion beam (see FIGS. 3 and 4). In such a case, each fluence element is associated with a scanning spot of the ion beam.

Alternatively, each treatment plan is configured to be delivered using a radiation beam collimated by an MLC. The MLC can be in the form of a binary configuration or continuous configuration. Each treatment plan can be configured to be delivered with the incidence direction of the radiation beam relative to the target volume changing during the course of the delivery.

Using the embodiments presented herein, the convex combination of treatment plans from the second set is directly deliverable, i.e. can be used directly in the treatment machine, which simplifies clinical decision making. Moreover, no post-processing after the MCO navigation is thus necessary to make the combination of plans deliverable. This is of great value, since post-processing can introduce errors and takes time to execute.

Figure 8:
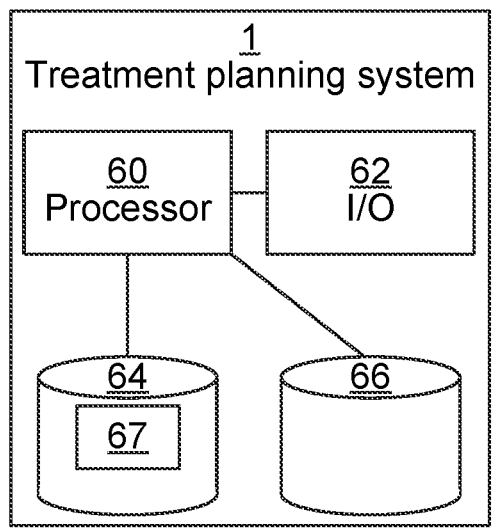
FIG. 8 is a schematic diagram illustrating components of the treatment planning system of FIG. 1 according to one embodiment.

FIG. 8 is a schematic diagram illustrating components of the treatment planning system of FIG. 1 according to one embodiment. A processor 60 is provided using any combination of one or more of a suitable central processing unit (CPU), multiprocessor, microcontroller, digital signal processor (DSP), application specific integrated circuit etc., capable of executing software instructions 67 stored in a memory 64, which can thus be a computer program product. The processor 60 can be configured to execute the method described with reference to FIG. 7 above.

The memory 64 can be any combination of random-access memory (RAM) and read only memory (ROM). The memory 64 also comprises persistent storage, which, for example, can be any single one or combination of magnetic memory, optical memory, solid-state memory or even remotely mounted memory.

A data memory 66 is also provided for reading and/or storing data during execution of software instructions in the processor 60. The data memory 66 can be any combination of random-access memory (RAM) and read only memory (ROM).

The treatment planning system 1 further comprises an I/O interface 62 for communicating with other external entities. Optionally, the I/O interface 62 also includes a user interface.

Other components of the treatment planning system 1 are omitted in order not to obscure the concepts presented herein.

Figure 9:
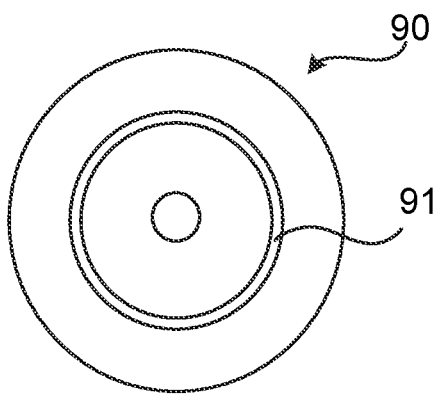
FIG. 9 shows one example of a computer program product comprising computer readable means.

FIG. 9 shows one example of a computer program product comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 64 of FIG. 8. While the computer program 91 is here schematically shown as a track on the depicted optical disk, the computer program can be stored in any way which is suitable for the computer program product, such as a removable solid-state memory, e.g. a Universal Serial Bus (USB) drive.

The aspects of the present disclosure have mainly been described above with reference to a few embodiments. However, as is readily appreciated by a person skilled in the art, other embodiments than the ones disclosed above are equally possible within the scope of the invention, as defined by the appended patent claims. Thus, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method for generating a plurality of treatment plans for radiation therapy, each treatment plan specifying weights for a plurality of geometrically defined fluence elements, each weight defining an amount of radiation fluence, to thereby provide radiation dose to a target volume, the method being performed in a treatment planning system and comprising the steps of:
   generating a first set of treatment plans;
   determining a subset of the fluence elements, based on the first set of treatment plans;
   generating a second set of at least two treatment plans, wherein the second set of treatment plans only contains the weights for the subset of fluence elements; and
   calculating, in an operator navigation system comprising a graphical user interface and a navigation control interface, a navigated dose distribution by interpolation of dose distributions associated with the second set of treatment plans.

2. The method according to claim 1, wherein a non-zero weight of a fluence element in the second set of treatment plans is greater than or equal to a minimum weight.

3. The method according to claim 1, wherein said generating a second set of at least two treatment plans includes applying a constraint that fluence elements not included in the determined subset of the fluence elements shall be zero.

4. The method according to claim 1, wherein the first set of treatment plans is a result of optimization with respect to a first multi-criteria optimization problem and the second set of treatment plans is a result of optimization with respect to a second multi-criteria optimization problem.

5. The method according to claim 4, wherein the second multi-criteria optimization problem differs from the first multi-criteria optimization problem by a constraint that fluence elements not included in the determined subset of the fluence elements shall be zero.

6. The method according to claim 1, wherein the graphical user interlace is operable to visualize the navigated dose distribution and the navigation control interface is operable to allow an operator to adjust the navigated dose distribution.

7. The method according to claim 1, wherein the step of determining a subset of the fluence elements comprises discarding fluence elements having a statistical measure less than a threshold weight, the statistical measure being calculated for each fluence element across all treatment plans in the first set of treatment plans.

8. The method according to claim 7, wherein the statistical measure comprises a mean value or a percentile value.

9. The method according to claim 1, wherein the step of determining a subset of the fluence elements comprises ensuring there is a sufficient density of the geometrically defined fluence elements across the target volume.

10. The method according to claim 9, wherein said ensuring there is a sufficient density of the fluence elements across the target volume includes:
computing a reference coverage;
determining an initial subset of the fluence elements; and
updating the initial subset of the fluence elements by repeatedly determining a subset of the fluence elements, until a verification can be made that the computed reference coverage is obtainable using the updated subset of the fluence elements.

11. The method according to claim 10, wherein the reference coverage includes a volume-at-dose.

12. The method according to claim 1, wherein each treatment plan is configured to be delivered using a scanned ion beam, wherein each fluence element is associated with a scanning spot of the beam, the scanning spot being defined by a scan position for the beam and a beam energy.

13. The method according to claim 1, wherein each treatment plan is configured to be delivered using a radiation beam collimated by a binary multi-leaf collimator, MLC, wherein each leaf of the MLC can alternate between an open and a closed position, wherein each fluence element is associated with a particular leaf of the MLC at a particular incidence direction of the beam relative to the target volume.

14. The method according to claim 13, wherein each incidence direction of the radiation beam relative to the target volume is determined based on a location of either or both of a rotating gantry and a moveable couch.

15. The method according to claim 13, wherein each treatment plan is configured to be delivered with the incidence direction of the radiation beam relative to the target volume changing during a course of the delivery.

16. The method according to claim 1, wherein each treatment plan is configured to be delivered using a radiation beam collimated by a multi-leaf collimator, MLC, wherein the leaves of the MLC are arranged into opposed leaf pairs and each leaf can assume any one of a plurality of positions between a minimum and a maximum position, wherein each fluence element is associated with a bixel, each bixel being a surface element in a cross-section of the beam at a particular incidence direction relative to the target volume.

17. A treatment planning system for generating a plurality of treatment plans for radiation therapy, each treatment plan specifying weights for a plurality of geometrically defined fluence elements, each weight defining an amount of radiation fluence, to thereby provide radiation dose to a target volume, the treatment planning system comprising:
a processor; and
a memory storing instructions that, when executed by the processor, cause the treatment planning system to:
generate a first set of treatment plans;
determine a subset of the fluence elements, based on the first set of treatment plans;
generate a second set of at least two treatment plans, wherein the second set of treatment plans only contains weights for the subset of fluence elements; and
calculate, in an operator navigation system comprising a graphical user interface and a navigation control interface, a navigated dose distribution by interpolation of dose distributions associated with the second set of treatment plans.

18. A computer program product for generating a plurality of treatment plans for radiation therapy, each treatment plan specifying weights for a plurality of geometrically defined fluence elements, each weight defining an amount of radiation fluence, to thereby provide radiation dose to a target volume, the computer program product comprising a non-transitory computer readable storage medium having program code embodied therewith which, when run on a treatment planning system causes the treatment planning system to:
generate a first set of treatment plans;
determine a subset of the fluence elements, based on the first set of treatment plans;
generate a second set of at least two treatment plans, wherein the second set of treatment plans only contains weights for the subset of fluence elements; and
calculate, in an operator navigation system comprising a graphical user interface and a navigation control interface, a navigated dose distribution by interpolation of dose distributions associated with the second set of treatment plans.

* * * * *